United States Patent [19]
Johnson et al.

[11] Patent Number: 6,119,522
[45] Date of Patent: *Sep. 19, 2000

[54] ELECTROMAGNETIC ACOUSTIC TRANSDUCER AND METHODS OF DETERMINING PHYSICAL PROPERTIES OF CYLINDRICAL BODIES USING AN ELECTROMAGNETIC ACOUSTIC TRANSDUCER

[75] Inventors: Ward L. Johnson, Gaithersburg, Md.; George A. Alers, Boulder, Colo.; Bertram A. Auld, Menlo Park, Calif.

[73] Assignee: The United States of America as represented by the Secretary of Commerce, Washington, D.C.

[*] Notice: This patent is subject to a terminal disclaimer.

[21] Appl. No.: 09/294,979

[22] Filed: Apr. 19, 1999

Related U.S. Application Data

[60] Continuation-in-part of application No. 09/157,082, Sep. 18, 1998, which is a division of application No. 08/285,018, Aug. 2, 1994, Pat. No. 5,895,856.

[51] Int. Cl.[7] .................................................. G01N 29/24
[52] U.S. Cl. .............................................. 73/643; 73/668
[58] Field of Search ............................. 73/643, 578, 576, 73/668, 573, 602, 622, 623, 650, 659

[56] References Cited

U.S. PATENT DOCUMENTS

| | | | |
|---|---|---|---|
| 4,248,092 | 2/1981 | Vasile et al. | 73/643 |
| 4,289,030 | 9/1981 | Alers et al. | 73/643 |
| 4,305,294 | 12/1981 | Vasile et al. | 73/643 |
| 4,450,725 | 5/1984 | Yamaguchi et al. | 73/643 |
| 4,466,287 | 8/1984 | Repplinger et al. | 73/643 |
| 5,895,856 | 4/1999 | Johnson et al. | 73/643 |

*Primary Examiner*—Helen C. Kwok
*Attorney, Agent, or Firm*—Holland & Hart LLP

[57] ABSTRACT

An electromagnetic acoustic transducer for inducing and sensing vibrations in a cylindrical object and methods of using an electromagnetic acoustic transducer to determine resonant frequencies and physical properties of cylindrical objects. The electromagnetic acoustic transducers produce specific modes of vibration in cylindrical objects including axial shear vibrations. The electromagnetic acoustic transducers are used to determine the temperature, dimensions, elastic constants, and damping coefficients of cylindrical objects, the magnitude of a load applied to a cylindrical object, or the texture or grain orientation of the material forming a cylindrical object.

15 Claims, 12 Drawing Sheets p=1 p=2 p=3 p=10

ELECTROMAGNETIC ACOUSTIC TRANSDUCER AND METHODS OF DETERMINING PHYSICAL PROPERTIES OF CYLINDRICAL BODIES USING AN ELECTROMAGNETIC ACOUSTIC TRANSDUCER

RELATED APPLICATIONS

This is a continuation of application Ser. No. 08/285,018, filed on Aug. 2, 1994 and now issued as U.S. Pat. No. 5,895,856 and a continuation of copending U.S. patent application Ser. No. 09/157,082, filed Sep. 18, 1998 both having the same inventors as this invention.

BACKGROUND

1. Field of the Invention

The invention relates to electromagnetic acoustic transducers usable with cylindrical objects, and methods for determining resonant frequencies and physical properties of cylindrical objects using electromagnetic acoustic transducers.

2. Summary of the Invention

The invention is directed to an electromagnetic acoustic transducer (hereinafter "EMAT") adapted for use with cylindrical objects, and to methods for using an EMAT to determine the resonant frequencies and physical properties of a cylindrical object. "Cylindrical object" is used to denote a body having a cylindrical shape with an approximately circular cross section. The term cylindrical body includes solid cylindrical bodies and hollow cylindrical bodies such as pipes and tubes.

The EMAT of this invention includes a housing having a circular opening, a plurality of magnets mounted in the housing at evenly spaced intervals around the circular opening, and at least one wire coil mounted in the housing adjacent the circular opening and the polar ends of the plurality of magnets. Applying an electrical excitation signal to a wire coil of the EMAT will excite vibrations in a cylindrical object inserted into the housing of the EMAT. When the excitation signal is at a resonant frequency of the cylindrical object, the cylindrical object resonates, i.e., the forces applied to the cylindrical body by the EMAT constructively interfere with the natural vibrations of the cylindrical body, and large amplitude vibrations are produced. Once the cylindrical object is vibrating, the EMAT of this invention is also able to sense the amplitude and frequency of the vibrations in the cylindrical object.

The EMAT of this invention excites very specific types of vibrational motion in the cylindrical object inserted into the circular opening. Depending on the orientation of the wire coil relative to the magnets and the cylindrical object the EMAT can induce axial shear vibrations, torsional vibrations, radial vibrations or plain strain vibrations.

The EMAT of this invention is also useful in determining the frequencies at which a cylindrical object experiences resonant vibrations in each of the above identified types of vibrational motion. In addition, various physical properties of the cylindrical object, or the loading applied to the cylindrical object can be determined by:

(1) determining the amount of time it takes for resonant vibrations in the cylindrical body to decrease to a negligible value;

(2) comparing resonant frequencies of the cylindrical object to resonant frequencies of a standardized cylindrical object made from the same material and having approximately the same dimensions;

(3) determining how the resonant frequencies of several types of vibrational motion change as a load is applied to the cylindrical object; and (4) determining how the amplitude of resonant vibrations change as the object is rotated within in the EMAT.

In particular, this invention provides a non-contact type EMAT usable with cylindrical objects.

This invention also provides an EMAT capable of exciting specific types of vibrational motion in the cylindrical object.

This invention further provides an EMAT capable of exciting axial shear vibrations, torsional vibrations, radial vibrations, or plain strain vibrations in a cylindrical object.

This invention provides a method for using an EMAT to determine the resonant frequencies of a cylindrical object.

This invention also provides a method for using an EMAT to determine the resonant frequency or a cylindrical object for axial shear vibrations, torsional vibrations, radial vibrations, or plain strain mode vibrations.

This invention further provides methods for using an EMAT to measuring physical properties of cylindrical objects.

This invention further provides a method for using an EMAT to determine the radial depth from the exterior surface of a cylindrical object at which physical properties of the material of the cylindrical object undergo a change.

This invention also provides a method for using an EMAT to determine the magnitude of a load placed on a cylindrical object.

This invention further provides a method for using an EMAT to determine the texture or grain orientation of the material forming a cylindrical object.

These and other objects and advantages of the present invention will become apparent from the following detailed description of preferred embodiments when taken in conjunction with the accompanying drawings.

3. BRIEF DESCRIPTION OF THE DRAWINGS

The invention will be described in detail with the reference to the following figures wherein like elements bear like reference numerals and wherein.

4. DETAILED DESCRIPTION OF THE PREFERRED EMBODIMENTS

Figure 1:
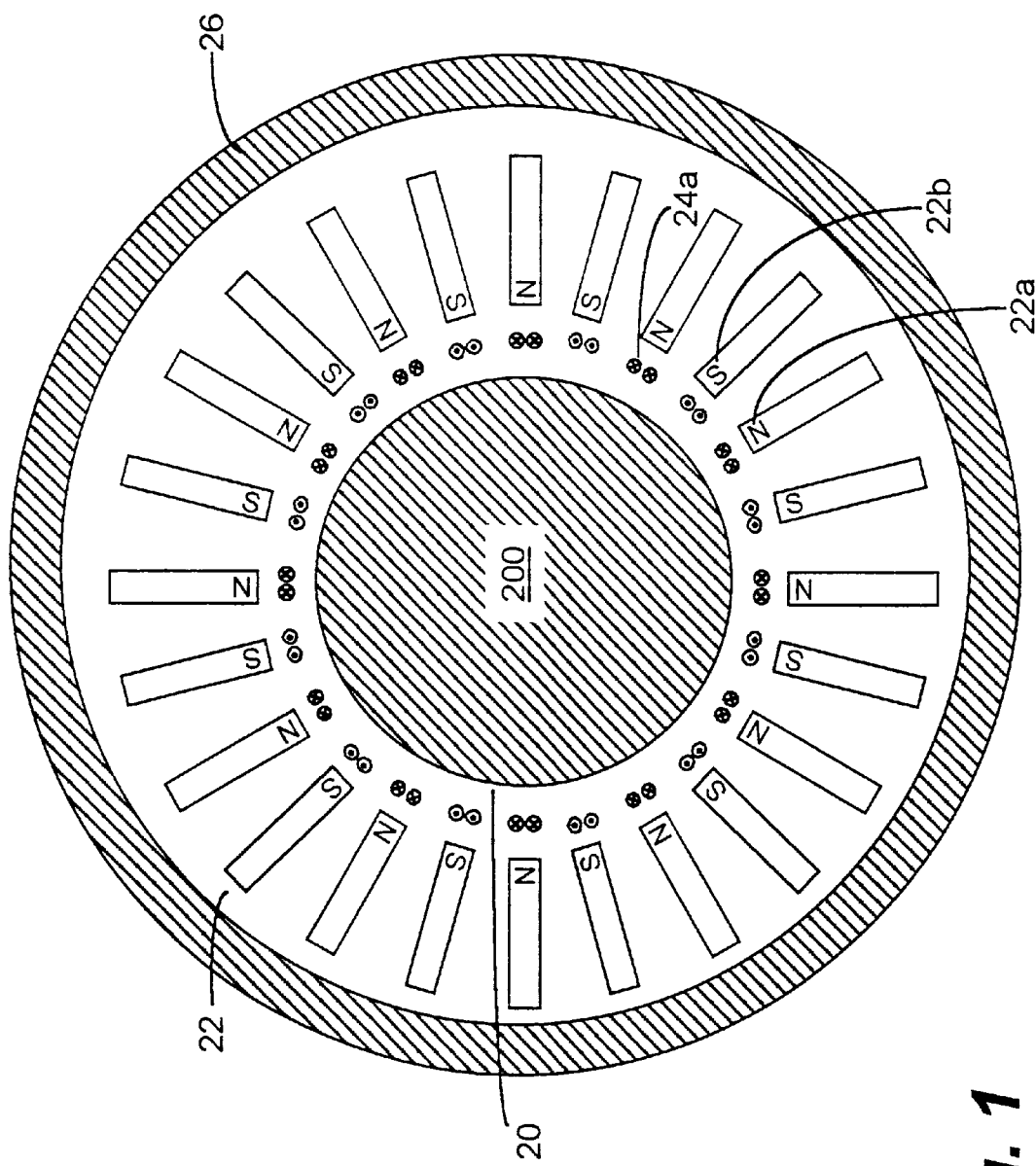
FIG. 1 is a sectional view of an electromagnetic acoustic transducer for exciting torsional vibrations in a cylindrical object.

FIG. 1 shows a first type of EMAT 100 capable of exciting torsional vibrations in a cylindrical object 200. The EMAT 100 comprises a housing 26 having a circular opening 20. A cylindrical object 200 is inserted into the circular opening 20. The cylindrical object 200 shown in FIG. 1 extends into and out of the page.

A plurality of magnets 22 are mounted in the housing 26 around the circular opening 20 at evenly spaced intervals. The polar ends 22a and 22b of the magnets 22 are adjacent the circular opening, and each part of adjacent magnets 22 has ends 22a and 22b of opposite polarity. The EMAT 100 also has at least one wire coil 24 which is also mounted in the housing 26 adjacent the circular opening 20. In this first type of EMAT 100, the individual wires 24a of the wire coil 24 are mounted adjacent to the polar ends 22a and 22b of the plurality of magnets 22, and are arranged in a meander pattern wherein the wires 24a extend back and forth through the circular opening 20 along the axial direction of the cylindrical object 200 (i.e. into and out of the page). The wires having an X in the center are extending out of the page, and the wires with a dot in the center are extending into the page.

Any type of cylindrical object 200 comprising an electrically conductive material can be used with the EMAT 100. As mentioned above, the cylindrical object 200 can be solid or hollow. When an electrical excitation signal is applied to the wire coil 24 a current begins to flow through the wires 24a. Because the wires 24a are located in the magnetic fields of the magnets 22, and because the cylindrical object 200 is also located adjacent the wire coil 24, eddy currents are induced in the cylindrical object 200. If the EMAT 100 is held in a fixed position the eddy currents in the cylindrical object 200, which are also in the presence of the magnetic field, create Lorentz forces that apply a force to the material of the cylindrical object 200 in a certain direction.

Because the current runs in a first direction through the wires 24a adjacent the north ends 22a of the plurality of magnets 22, and the current runs in an opposite direction in the wires 24a adjacent the south ends 22b of the plurality of magnets 22, the Lorentz forces resulting from the application of a voltage to the wire coil 24 will always be oriented in the same direction. For the configuration shown in FIG. 1, the Lorentz forces will cause a torsional force twisting the cylindrical object 200 in a rotational direction.

If the electrical excitation signal applied to the wire coil 24 is an alternating current, the Lorentz forces applied to the cylindrical object 200 will also alternate. As a result, the cylindrical object 200 will first twist in one direction, then twist in the opposite direction as the current alternates. If the frequency of the alternating excitation signal applied to the wire coil 24 matches a resonant torsional vibrational frequency of the cylindrical object 200, the torsional forces applied by the EMAT 100 will constructively interfere with the vibrational movement of the cylindrical object 200, and the cylindrical object 200 will resonate.

Figure 2:
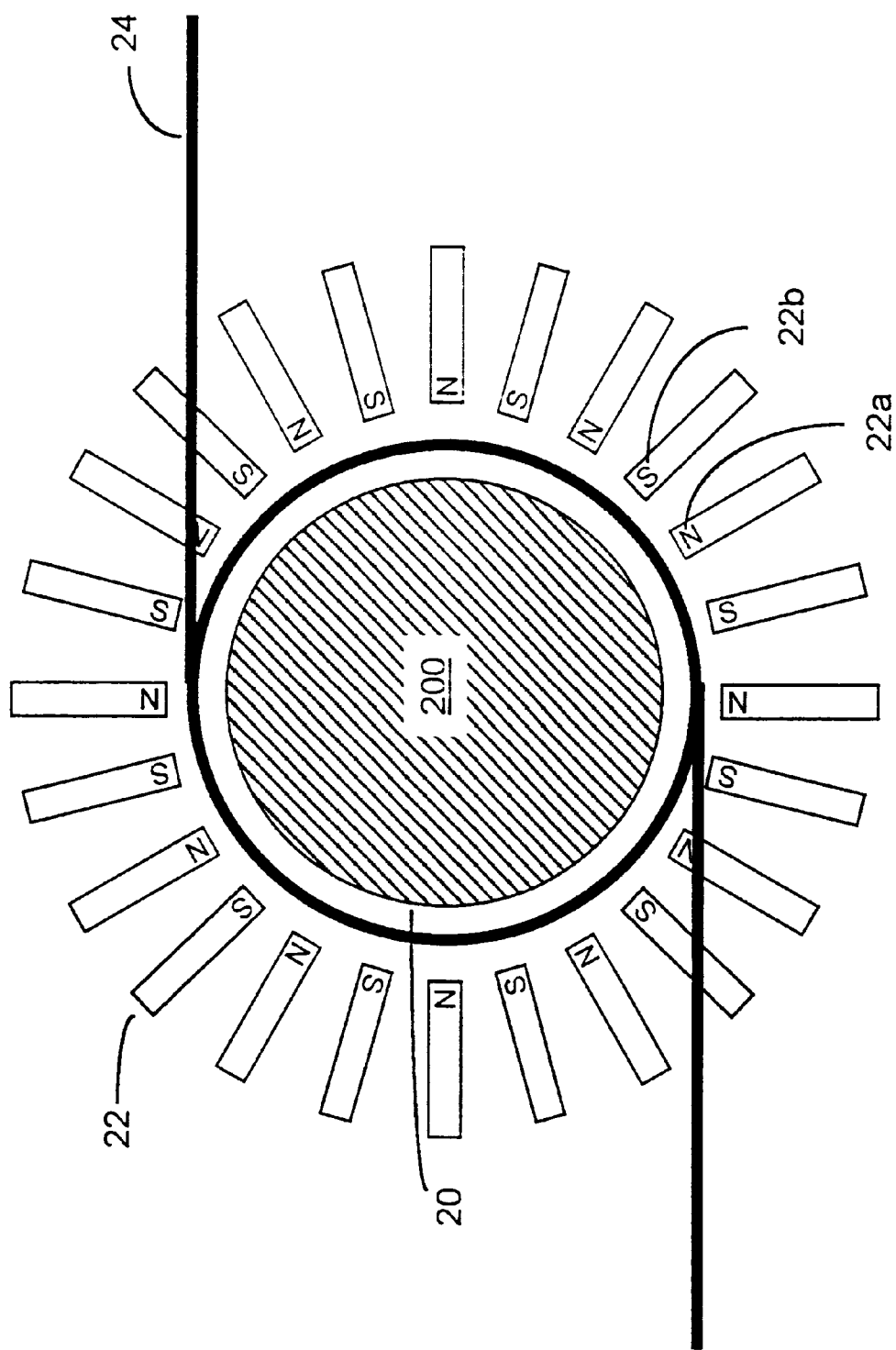
FIG. 2 is a sectional view of an electromagnetic acoustic transducer for exciting axial shear vibrations in a cylindrical object.

FIG. 2 shows a second type of EMAT 100 capable of exciting axial shear vibrations in the cylindrical object 200. As in the first type of EMAT 100 described above, the wire coil 24 of the second type of EMAT 100 is also mounted adjacent the circular opening 20 in the housing 26. In this second type of EMAT 100, however, the wire coil 24 is wound around the circular opening 20 in the form of a solenoid coil. Applying an electrical excitation signal to the wire coil 24 will cause Lorentz forces in the cylindrical object 200 that are oriented in the axial direction of the cylindrical object 200. In other words, the forces will be directed into and out of the page.

Because the current always runs in the same direction relative to the cylindrical object 200, and because the wire coil 24 passes next to alternating poles 22a and 22b of the plurality of magnets 22, the current causes alternating direction Lorentz in the cylindrical object 200. When the current is flowing through the wire coil 24 in a first direction, the Lorentz force adjacent a south end 22b of a magnet 22 will be directed out of the page and the Lorentz force adjacent a north end 22a of a magnet 22 will be directed into the page. When the direction of the current flowing through the wire 24 is reversed, the Lorentz forces will also reverse. Applying an alternating current to the wire coil 24 will create alternating axial Lorentz forces in the cylindrical object 200. By adjusting the frequency of the electrical excitation signal applied to the wire coil 24, the cylindrical object 200 can be induced to vibrate at a resonant frequency for axial shear vibrations.

Figure 16:
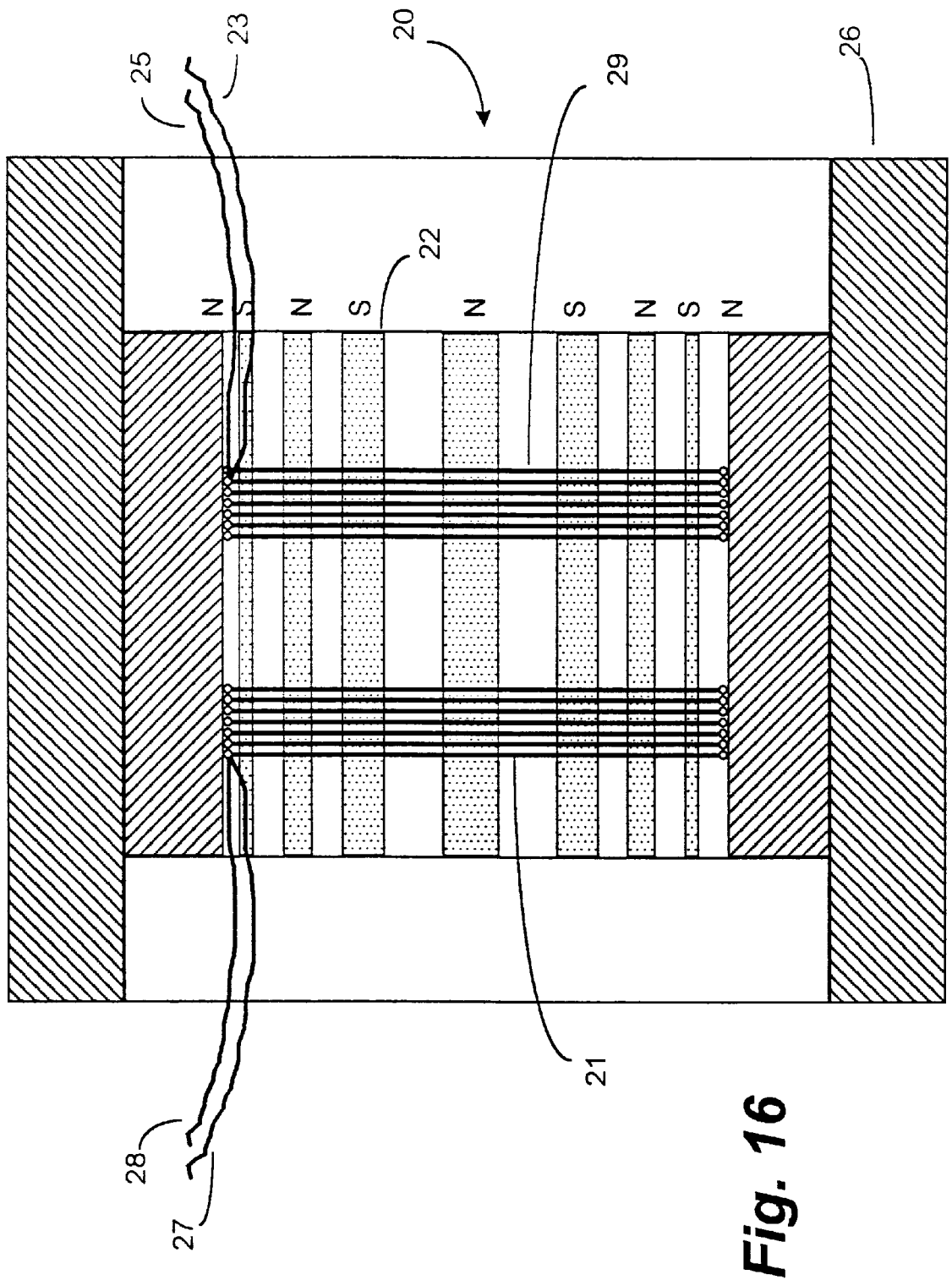
FIG. 16 is a cross-section of an electromagnetic acoustic transducer according to the present invention having two wire coils.

FIG. 16 shows an axial cross-sectional view of the second type of EMAT 100. The EMAT 100 has a hollow cylindrical housing 26, in which the plurality of magnets 22 are mounted. The plurality of magnets 22 are mounted at evenly spaced intervals around the inside of the cylindrical housing 26 so that a cylindrical opening 20 extends through the longitudinal axis of the EMAT 100. The EMAT 100 has two wire coils 21 and 29 which are mounted in the EMAT 100 adjacent the polar ends 22a and 22b of the plurality of magnets 22. The wire coils 21 and 29 form a circle around the cylindrical opening 20 in the center of the EMAT 100. The first wire coil 21 has a first end 27 and a second end 28. The second wire coil 29 has a first end 25 and a second end 23.

Figure 3:
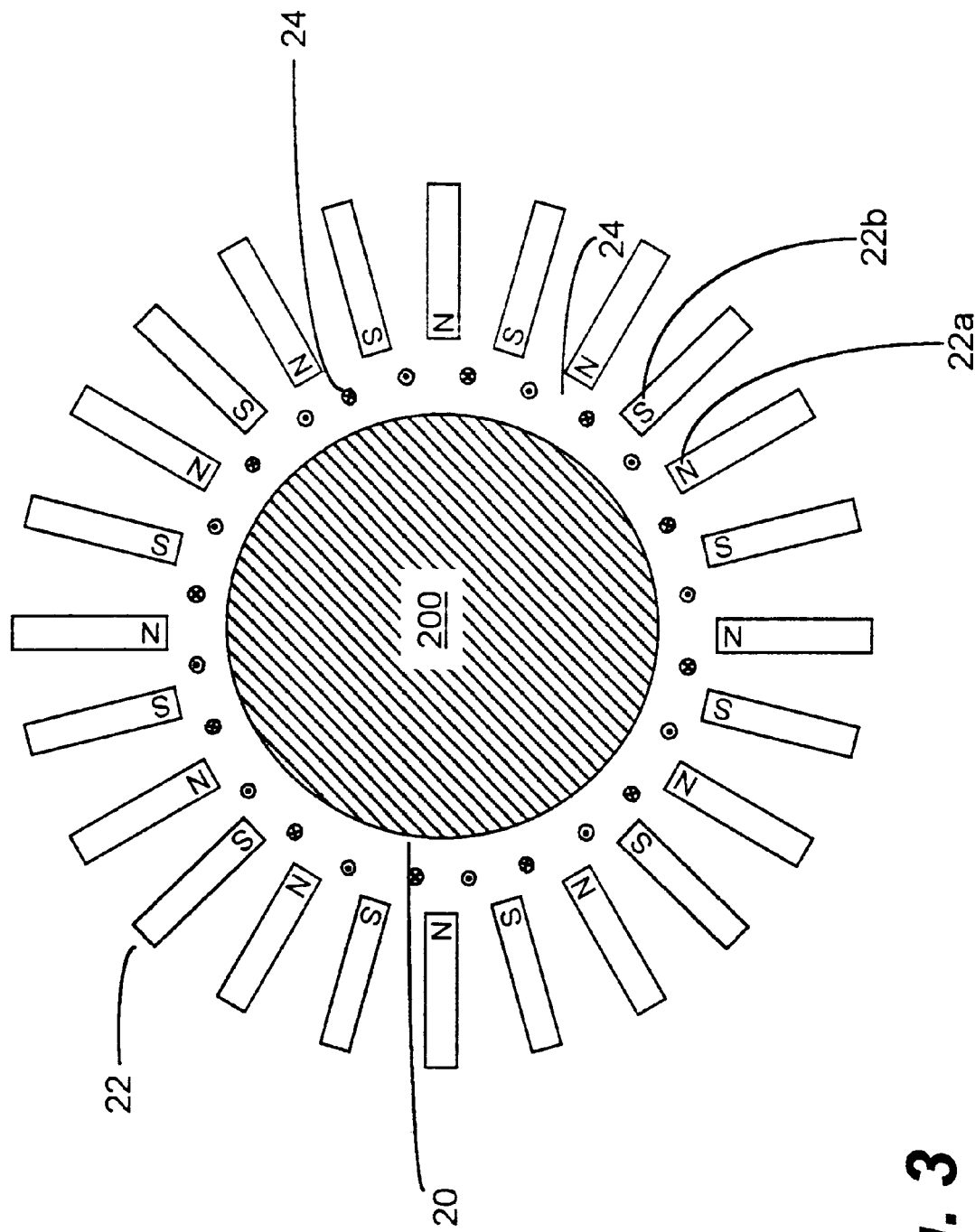
FIG. 3 is a sectional view of an electromagnetic acoustic transducer for exciting radial vibrations in a cylindrical object.

FIG. 3 shows a third type of EMAT 100 capable of inducing radial vibrations in the cylindrical object 200. In this third type of EMAT 100, the wire 24a of the wire coil 24 are located between adjacent ends 22a and 22b of adjacent magnets 22, and the wire coil 24 is disposed in a meander pattern extending into and out of the page as described above for the first type of EMAT 100. A voltage applied to the wire coil 24 will create Lorentz forces in the cylindrical object 200 which tend to pull the material of the cylindrical object 200 outward in a radial direction or push the material of the cylindrical object inward in a radial direction. Because a current passing through the wire coil 24 will run in a first direction for wires having a north pole 22a of a magnet 22 on the left and a south pole 22b of a magnet 22 In the right and because the current will run in the opposite direction for wires having a south pole 22b of a magnet 22 on the left and a north pole 22a of a magnet 22 on the right, the Lorentz forces applied to the cylindrical object 200 by the wires 24a of the wire coil 24 will always be oriented in the same radial direction (either into the center, or away from the center). Applying a current running in a first direction through the wire coil 24 will create Lorentz forces tending to pull the cylindrical object 200 outward in a radial direction. Reversing the current will cause the Lorentz forces to reverse, tending to push the cylindrical object 200 inward toward the central axis of the cylindrical object 200. Applying an alternating current to the wire coil 24 will cause alternating Lorentz forces which pull outward in the radial direction, then push inward in the radial direction. The frequency of an alternating current excitation signal applied to the wire coil 24 can be adjusted so that the cylindrical object 200 vibrates at a resonant frequency.

Each of the EMATs 100 described above excite specific types of vibrational motion in the cylindrical object 200. In each case, the actual vibrations caused by the EMATs 100 are only approximate. In other words, the first type of EMAT 100 described above is intended to produce only torsional vibrations. In practice the vibrations are not strictly limited to torsional motion. The vibrations are, however, close enough to pure torsional vibrations that they can be modeled as torsional vibrations for the purposes of analyzing the properties of the cylindrical object 200. The same is true for axial shear and radial vibrations for the second and third types of EMATs 100.

The term "plane strain vibrations" is used to denote vibrations in a cylindrical object which have no axial component. Torsional vibrations and radial vibrations are two variants of plane strain vibrations. Other types of plane strain vibrations are possible and may be useful for determining certain properties of the cylindrical object 200.

An EMAT 100 as described above can be used to determine the resonant frequencies and the physical properties of the cylindrical object 200 according to the following methods. The EMATs used in the methods described below, however, need not be one of the types described above. In each of the configurations described above, the wire coil 24 and the magnets 22 of the EMAT 100 were mounted in the housing 26 located around the exterior of the cylindrical object 200. The methods for determining the resonant frequency and the physical properties of the cylindrical object 200 described below are equally applicable to other types of EMATs, such as those designed to be inserted into the center of a hollow tube. The EMATs usable with hollow tubes could have both the wire coil 24 and the magnets 22 located inside the tube, or the magnets 22 could be located on one side of the tubing wall, and the wire coil 24 on the opposite side. The use of the methods described below is not intended to be limited to EMATs having any particular configuration.

Figure 4:
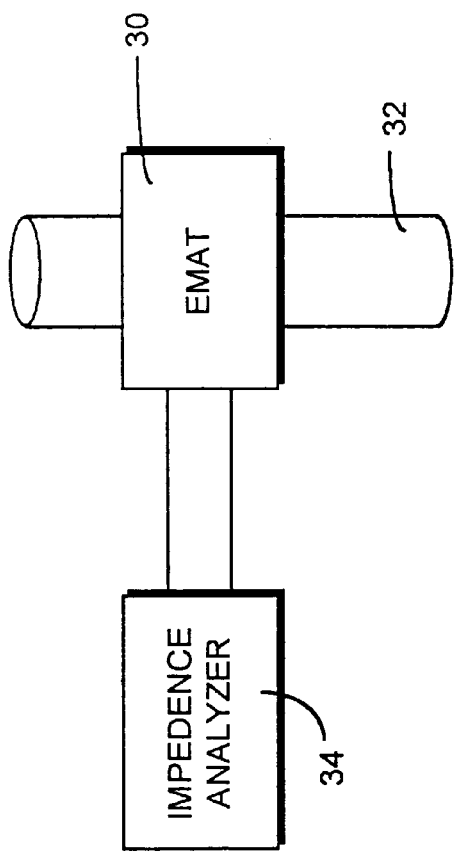
FIG. 4 is a block diagram of a first test apparatus for determining the resonant frequency of a cylindrical object using an electromagnetic acoustic transducer.

FIG. 4 shows a first type of test apparatus for determining a resonant frequency of a cylindrical object. The test apparatus comprises an impedance analyzer 34 attached to the wire coil of an EMAT 30. The EMAT 30 is attached to a cylindrical object 32. The EMAT could be one of the first, second or third types shown in FIGS. 1, 2 and 3, or any other type of EMAT designed to excite a specific type of vibration in the cylindrical object 32.

The impedance analyzer 34 applies an alternating current excitation signal to the wire coil of the EMAT 30 to excite a certain type of vibration in the cylindrical object 32. The vibrations in the cylindrical object 32, in turn, affect the impedance characteristics of the wire coil of the EMAT 30. The impedance characteristics of the wire coil of the EMAT 30 can be used to indicate resonant frequencies of the cylindrical object 32.

If the frequency of the excitation signal applied to the wire coil is gradually increased, as the frequency of the excitation signal passes through a resonant frequency of the cylindrical object 32, the amplitude of the real and imaginary parts of the impedance of the wire coil will experience local extreme. Depending on the electrical characteristics of the EMAT 30, the real or imaginary parts of the impedance of the wire coil 24 could experience a maximum or a minimum at the resonant frequency, or the amplitude of the real or imaginary parts of the impedance could experience a maximum just below the resonant frequency, followed by a minimum just above the resonant frequency, tracing out a Z-shape around the resonant frequency. A programmable impedance analyzer 34 can be programmed to gradually vary the frequency of an electrical excitation signal applied to the wire coil of the EMAT 30 and to note those frequencies at which the real or imaginary parts of the impedance experience extreme, thus indicating a resonant frequency of the cylindrical object 32.

Figure 8:
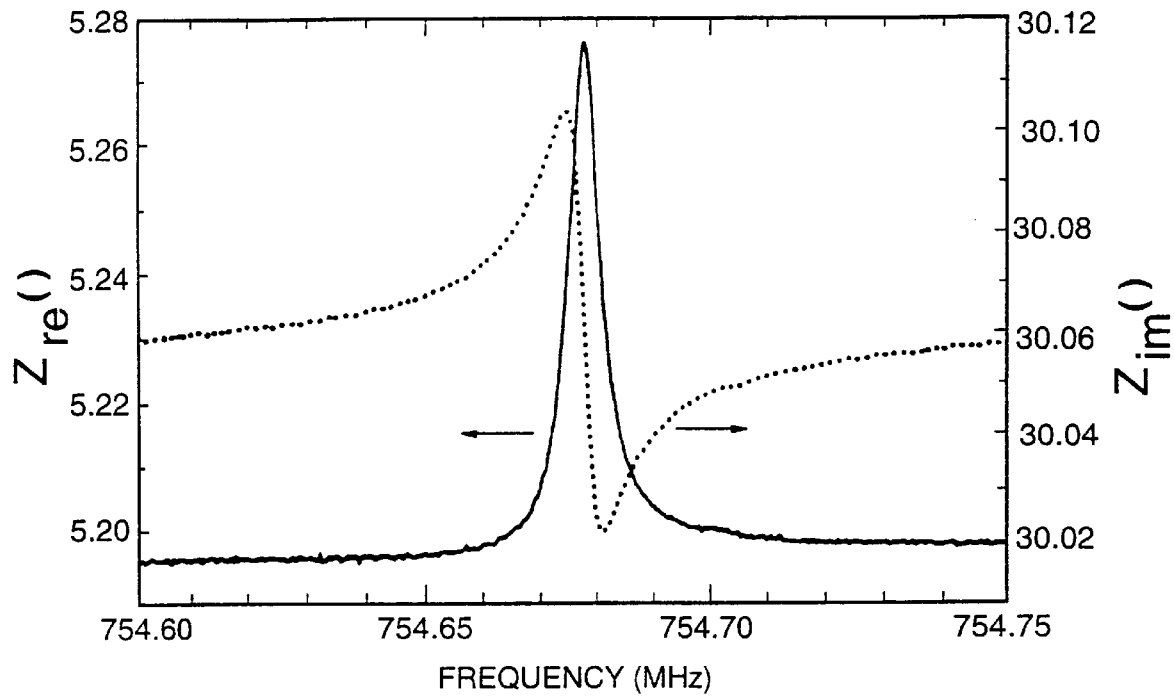
FIG. 8 is a chart showing the real and imaginary parts of the impedance of a wire coil of an electromagnetic acoustic transducer at various frequencies.

FIG. 8 shows a plot of the real and imaginary parts of the impedance of the wire coil of the EMAT 30 over a portion of the frequency band that includes a resonant frequency. As shown in FIG. 8, the real part of the impedance of the wire coil, shown as a solid line, experiences a sudden maximum at the resonant frequency. The imaginary part of the impedance, shown as a dotted line, trace a Z-shaped pattern around the resonant frequency.

The test apparatus described above can be used with an EMAT 30 having a single wire coil, or plural wire coils. If the EMAT 30 has a single wire coil, the impedance analyzer 34 applies an electrical excitation signal to the wire coil and senses the impedance of the same wire coil. If the EMAT 30 has first and second wire coils, the impedance analyzer 34 can apply an excitation signal to a first wire coil, and determine an impedance transfer function between the first and second wire coils.

Figure 5:
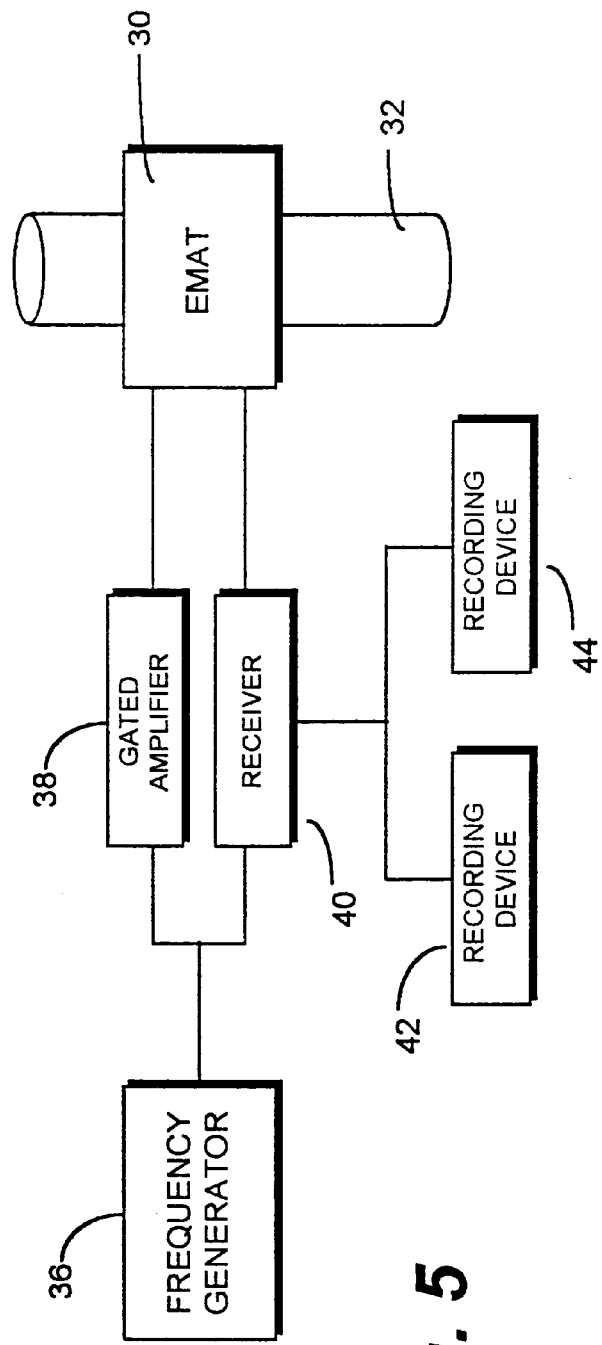
FIG. 5 is a block diagram of a second test apparatus for determining the resonant frequency of a cylindrical object using an electromagnetic acoustic transducer.

FIG. 5 shows a second type of test apparatus for determining the resonant frequencies of the cylindrical object 32. In this second type of test apparatus, a frequency generator 36 provides a frequency signal to a gated amplifier 38 and a receiver 40. The gated amplifier 38 provides an alternating current electrical excitation signal to the wire coil of an EMAT 30. The receiver 40 is connected to the EMAT 30 and senses an electrical response signal induced in wire coil of the EMAT 30 by vibrations in the cylindrical object 32. The receiver is also connected to a recording device 42 for recording the response signal, and an oscilloscope 44 for displaying the response signal.

In this second type of test apparatus, an alternating current electrical excitation signal is applied to wire coil of the EMAT 30 to induce vibrations in the cylindrical object 32. After a period of time the excitation signal is removed from the wire coil and the cylindrical object 32 is allowed to freely vibrate. Vibrations in the cylindrical object 32 will excite an alternating current in wire coil of the EMAT 30 for the same reasons the excitation signal produced vibrations in the first place. The EMAT 30 is essentially working in reverse.

After the excitation signal is removed from the wire coil, the receiver 40 is used to sense any electrical response signal generated in wire coil of the EMAT 30 by the vibrations of the cylindrical object 32. When the excitation signal applied to the wire coil of the EMAT 30 by the amplifier 38 is at a non-resonant frequency, the amplitude of the vibrations induced in the cylindrical object 32 will be relatively small, and the amplitude of the response signal will be correspondingly small. When an excitation signal applied to the EMAT 30 by the amplifier 38 is at or near a resonant frequency of the cylindrical object 30, the amplitude of the vibrations induced in the cylindrical object 32 will be relatively large, and the amplitude of the response signal induced in the EMAT 30 by the vibrations will be corresponding large.

Figure 7:
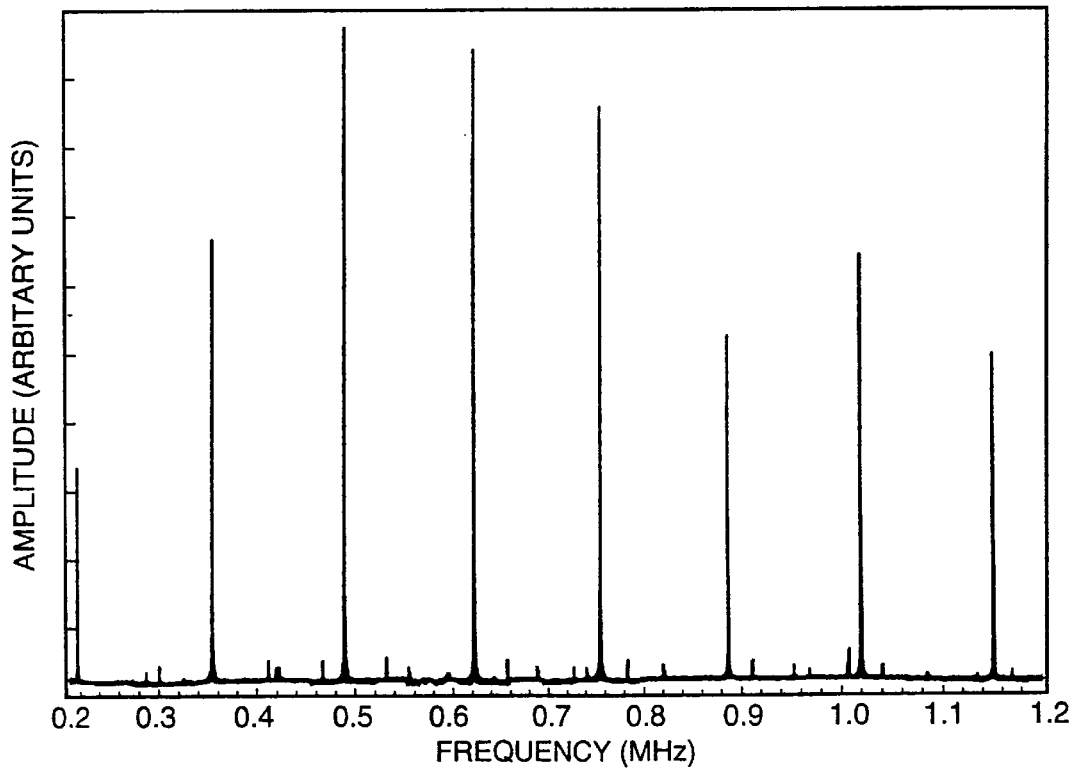
FIG. 7 is a chart showing the amplitude of vibrations of a cylindrical object at different frequencies.

By applying a plurality of excitation signals to the wire coil of the EMAT 30 at different frequencies, and sensing the response signal generated in the EMAT 30 by the vibrations occurring after each excitation, the resonant frequencies of the cylindrical object 32 can be determined. FIG. 7 shows a diagram of the amplitude of the response signal generated in the wire coil of the EMAT 30 by vibrations in the cylindrical object 32 following excitation at different frequencies. The amplitude of the response signal experiences a sharp maximum spike at the resonant frequencies of the cylindrical object.

As in the first test apparatus, the EMAT 30 used in the second test apparatus can have one or more wire coils. If the EMAT 30 has only a single wire coil the electrical excitation signal is applied to the single wire coil by the gated amplifier 38 for a period of time, then the excitation signal is removed and the receiver 40 senses a response signal induced in the wire coil.

Alternately, if the EMAT 30 is provided with first and second wire coils, the Hated amplifier 38 can be connected to the first wire coil, and the receiver 40 can be connected to the second wire coil. In this set up, the gated amplifier 38 applies an excitation signal to the first wire coil for a period of time to induce vibrations in the cylindrical object 32, then the excitation signal is removed. The receiver 40 is used to sense an response signal in the second wire coil after the excitation signal is removed.

The first and second wire coils can be physically separated. The only requirement is that vibrations excited by the first wire coil travel along the cylindrical body 32 and cause an excitation signal at the second wire coil. In addition, a first EMAT 30 can be used to excite vibrations in the cylindrical body, and a second EMAT 30 can be used to sense vibrations in the cylindrical body. Using two EMATs 30, one for exciting and one for sensing, is analogous to using a single EMAT having two wire coils. For the purposes of this description and the claims, the two methods are considered equivalents.

Figure 6:
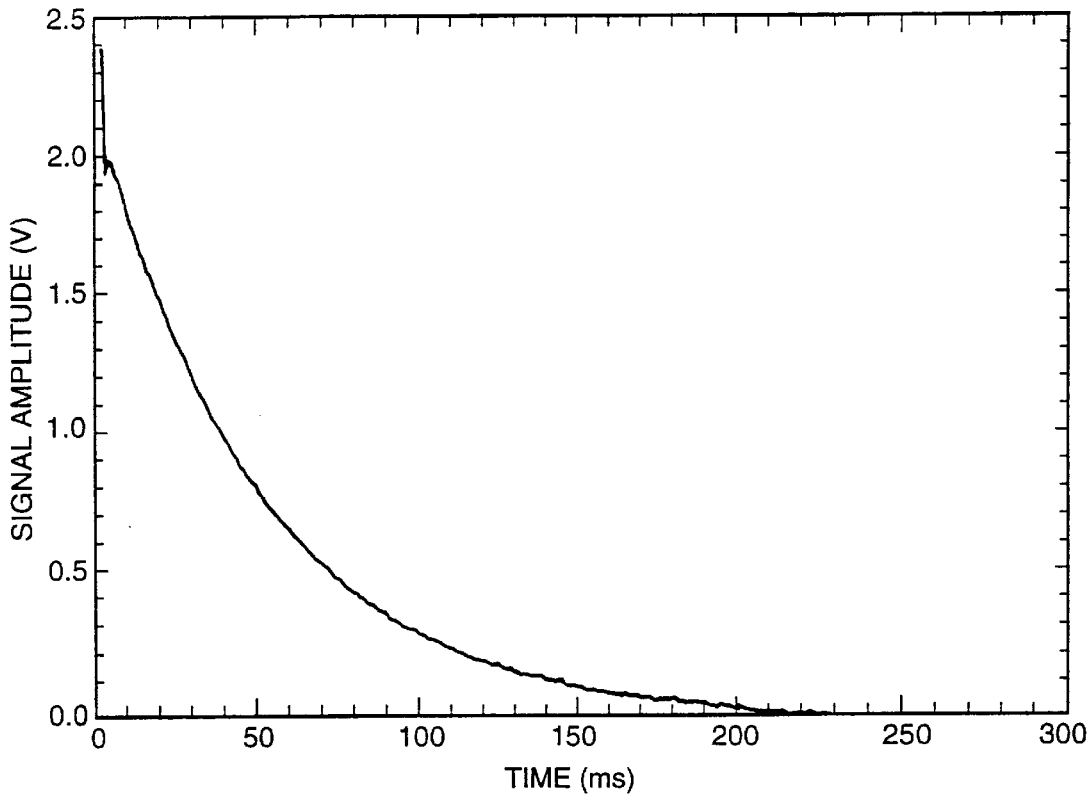
FIG. 6 is a chart showing the amplitude of vibrations in a cylindrical object over a period of time.

FIG. 6 shows the results of a first method for determining physical properties of a cylindrical object using the EMAT 30. In the first method, an excitation signal is applied to the EMAT 30 to excite the cylindrical object 32 to vibrate at a resonant frequency. The excitation signal is then removed, and the cylindrical object 32 is allowed to vibrate freely. The amplitude of an electrical response signal generated in the wire coil of the EMAT 30 by the resonant vibrations of the cylindrical object 32 is sensed using either of the two test set ups described above.

The amplitude of the response signal will gradually decrease over a period of time as the free vibrations are damped by the material of the cylindrical object 32. FIG. 6 shows a diagram Of the amplitude of a response signal generated in the EMAT 30 by free vibrations of the cylindrical object 32 over a period of time. The amount of time taken for the amplitude of the response signal to decrease to a negligible value can be used to determine the damping coefficient for the cylindrical object 32.

The frequencies at which the cylindrical object 32 resonates can also be used to determine the temperature of the cylindrical object 32. Changes in the temperature affect the frequency at which the cylindrical object 32 resonates. By determining the frequency of resonant vibrations for a particular-sized cylindrical object 32 formed from a particular material at a variety of different temperatures, a chart describing the relationship between temperature and resonant frequency can be constructed. Once the relationship is known, determining the resonant frequency will permit the determination of the temperature of the object 32.

The diameter of the cylindrical object 32 can also be determined using the EMAT 30. As described above for temperature, the diameter of the cylindrical object 32 affects its resonant frequency. For similarly-sized cylindrical object 32 formed from the same material, a slight change in the diameter will result in a slight change in the resonant frequencies. By determining the resonant frequencies of different diameter cylindrical objects 32 at a particular temperature, the relationship between the diameter and the resonant frequency at that temperature can be determined. Once the relationship is known, determining the resonant frequency of the cylindrical object 32 allows one to determine the diameter.

Likewise, the same method can be used to determine the relationship between resonant frequency and the wall thickness of tubing or piping. Once the relationship is known, determining the resonant frequency allows one to determine the wall thickness of the tubing or piping.

The number of magnets 22 used in the EMAT 30 to produce torsional vibrations or radial vibrations does not affect the frequencies at which the cylindrical object 32 resonates. These types of EMATs 30 are designed so that the forces applied to the cylindrical object 32 are relatively uniform around the circumference of the cylindrical object 32. What is important for these types of EMATs 30 is that enough magnets 22 are provided to apply a uniform force around the circumference of the cylindrical object 32.

However, the number of magnets 22 used in the EMAT 30 to induce axial shear vibrations (as described above for FIG. 2) does have an affect on the frequencies at which the cylindrical body 32 resonates. For a particular axial shear type EMAT 30, several different excitation frequencies will produce resonant vibrations in the cylindrical object 32.

Figure 9A:
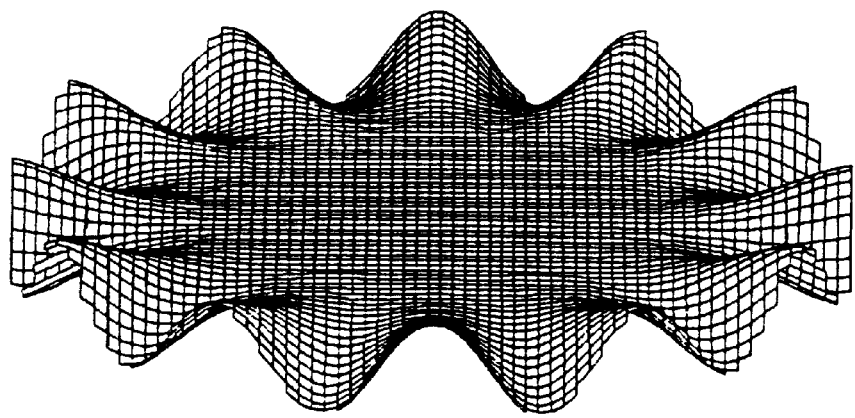
FIGS. 9A–9D are diagrams showing the displacement of a cross-section of a cylindrical object undergoing resonant axial shear vibrations.

FIG. 9A shows a cross-section of the cylindrical object 32 resonating at a first resonant frequency. Each wave peak of the diagram could be located adjacent the north pole 22a of a magnet, and each wave trough of the diagram could be located adjacent the south pole 226 of a magnet 22. At the resonant frequency, the Lorentz forces constructively interfere with the natural vibrations of the cylindrical object 32 to produce the standing waves shown in FIG. 9A. Changing the number of magnets 22 alters the number of peaks and troughs of the standing waves, thus altering the frequency of the resonant vibration.

Figure 9B:
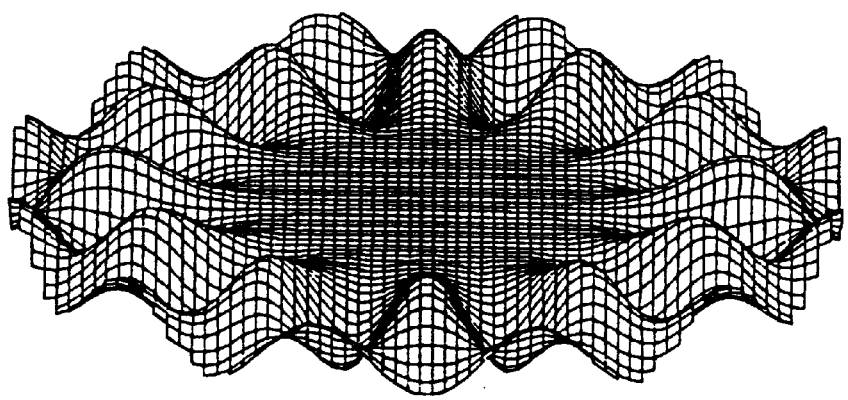
Figure 9C:
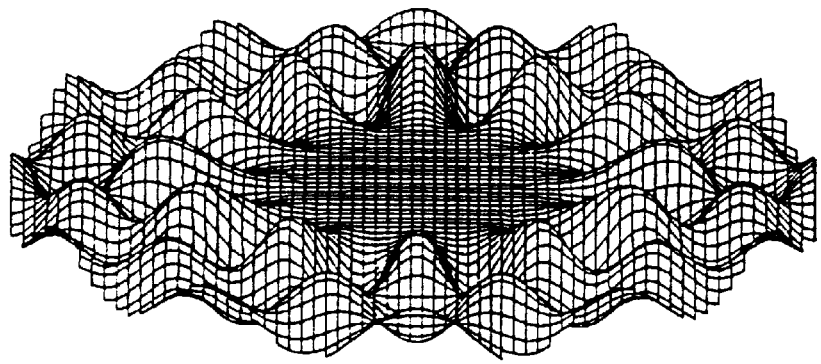
Figure 9D:
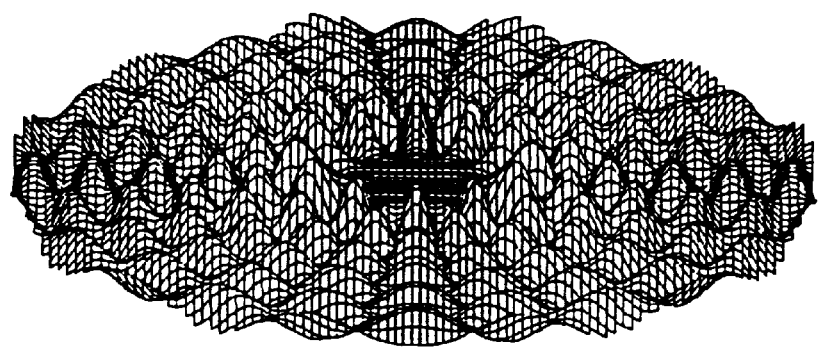

FIG. 9A represents the wave pattern in the material of the cylindrical object 32 when it is resonating at a first resonant frequency. FIG. 9B represents the wave pattern of the material of the cylindrical object 32 at a second, higher, resonant frequency. Likewise, FIGS. 9C and 9D represent the wave pattern in the material of the cylindrical object 32 at additional higher resonant frequencies. As shown in FIGS. 9A–9D, the higher the resonant frequency, the deeper towards the center of the cylindrical object 32 the vibrations penetrate. Because the depth of penetration of the vibrations varies for different resonant frequencies, the axial shear mode resonant frequencies can be used to measure the depth at which physical properties of the cylindrical object 32 undergo a change.

As in the method of temperature determination described above, for a cylindrical object 32 formed from a particular size and material, changing the physical properties of the material will change the resonant frequencies of the cylindrical object 32. Because axial shear vibrations penetrate to varying radial depths, the change in axial shear frequency of the cylindrical object 32 can be exploited to determine the radial depth at which the material properties change.

Figure 10:
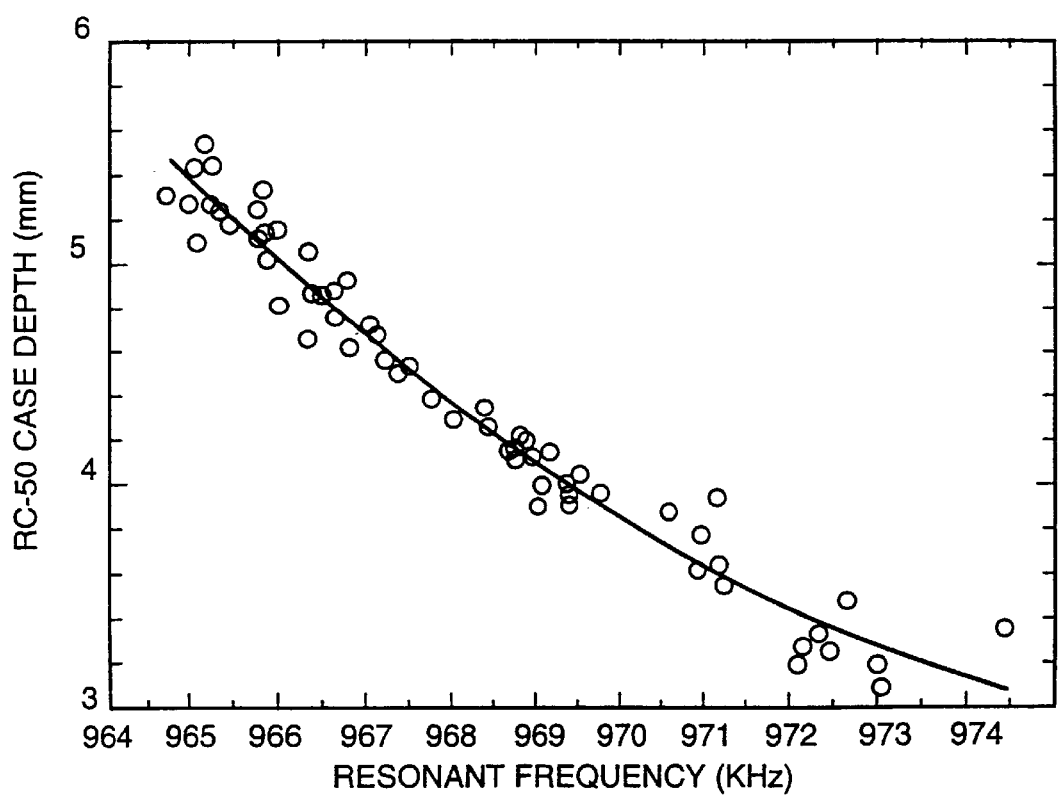
FIG. 10 is a chart showing the relationship between case hardening depth and the resonant frequency of a cylindrical object.
Figure 11:
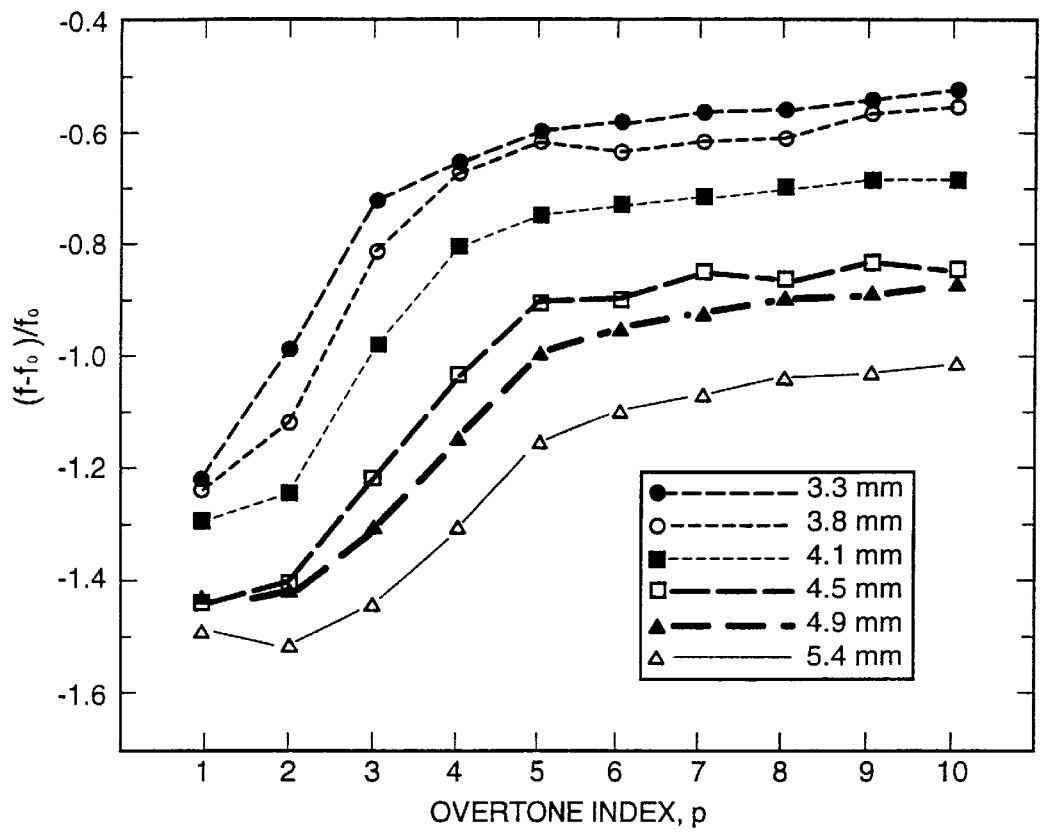
FIG. 11 is a chart showing the ratio between the resonant frequency for a case hardened cylindrical object to the resonant frequency of an unhardened cylindrical object for different resonant frequencies.
Figure 12:
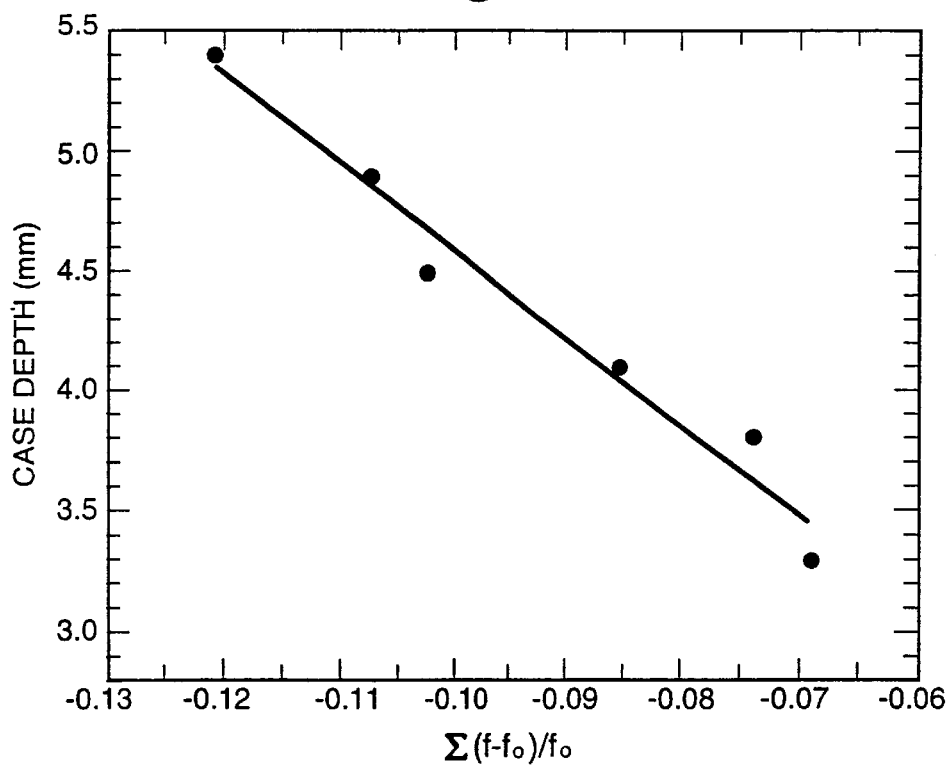
FIG. 12 is a chart showing the relationship between case hardening depth of a cylindrical object and the average of the ratios shown in FIG. 10.

Methods used to determine the case hardening depth of a cylindrical object are described in reference to the FIGS. 10, 11, and 12.

In a first method, the EMAT 30 was used to determine a single resonant frequency for axial shear vibrations for a plurality of different cylindrical objects 32. Each of the plurality of cylindrical objects 32 had similar dimensions and were formed from the same material. The case hardening depth, however, was different for each cylindrical object 32. FIG. 10 shows the change in the resonant frequency for different case hardening depths. Once a chart as in FIG. 10 is constructed, determining the resonant frequency of the cylindrical object 32 permits determination of the case hardening depth.

A second method for determining the case hardening depth is described in reference to FIGS. 11 and 12. In the second method, the EMAT 30 is used to determine a plurality of frequencies at which a first isotropic cylindrical object 32 (i.e. an object having homogeneous physical properties throughout the object) having no case hardening experiences resonant axial shear vibrations. Next, six cylindrical objects formed from the same material and having nearly identical dimensions were tested to determine the frequencies at which they experienced resonant vibrations. Each of the six cylindrical objects had been case hardened to a different radial depth. Because the case hardening altered the physical properties of each of the cylindrical objects, each cylindrical object 32 had different resonant frequencies for axial shear vibrations.

Next, for each of the cylindrical objects 32, ratios were calculated for each resonant axial shear mode. The ratios represented the change in a resonant frequency between the isotropic object and the hardened object, divided by the resonant frequency of the isotropic object. The ratios were then plotted as shown in FIG. 11. Finally, an average was calculated for each hardened cylindrical object representing the average of the ratios shown in FIG. 11. The average of the ratio values are plotted as shown in FIG. 12. As shown in FIG. 12, the average ratio values generally correspond to a straight line representing the relationship between case hardening depth and the average of the frequency shift ratios.

The above-described methods can be used to develop charts, as shown in FIGS. 10 and 12, for any set of cylindrical objects 32 having a variation in the physical properties of the material as a function of the radial depth. In addition, the same basic methods could be used to map the value or a physical material property as a function of radial penetration depth for a single cylindrical object 32. For instance, measuring the various axial shear resonant frequencies of the cylindrical object 32 with the EMAT 30 permits mapping the elastic constant of the cylindrical object 32 as a function of radial depth.

Figure 13:
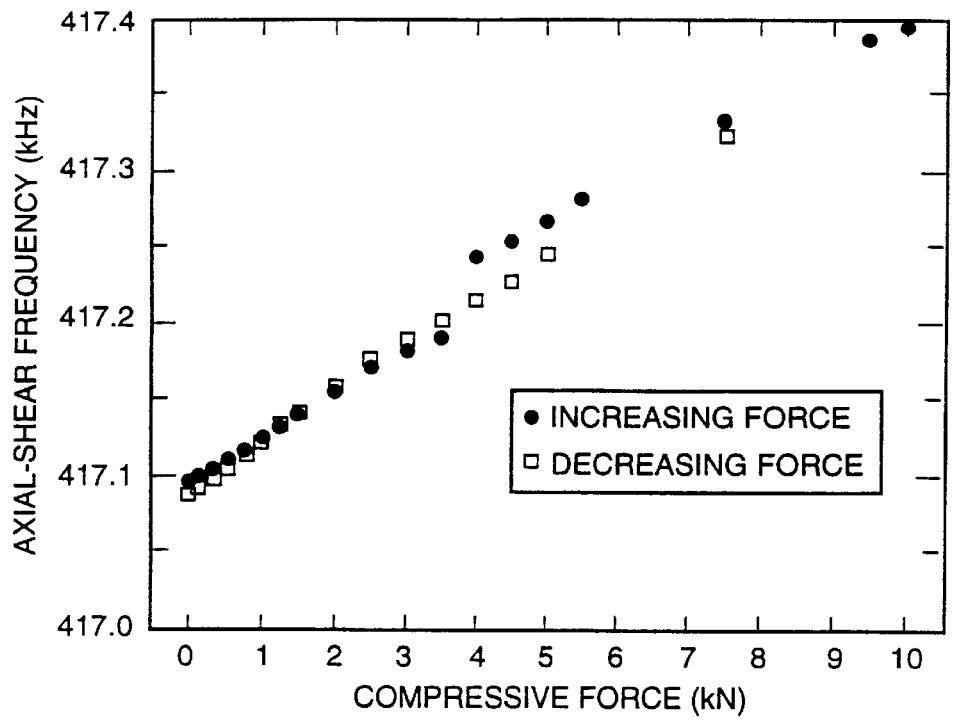
FIG. 13 is a chart showing the relationship between the resonant axial shear frequency and the magnitude of an axial load placed on a cylindrical object.
Figure 14:
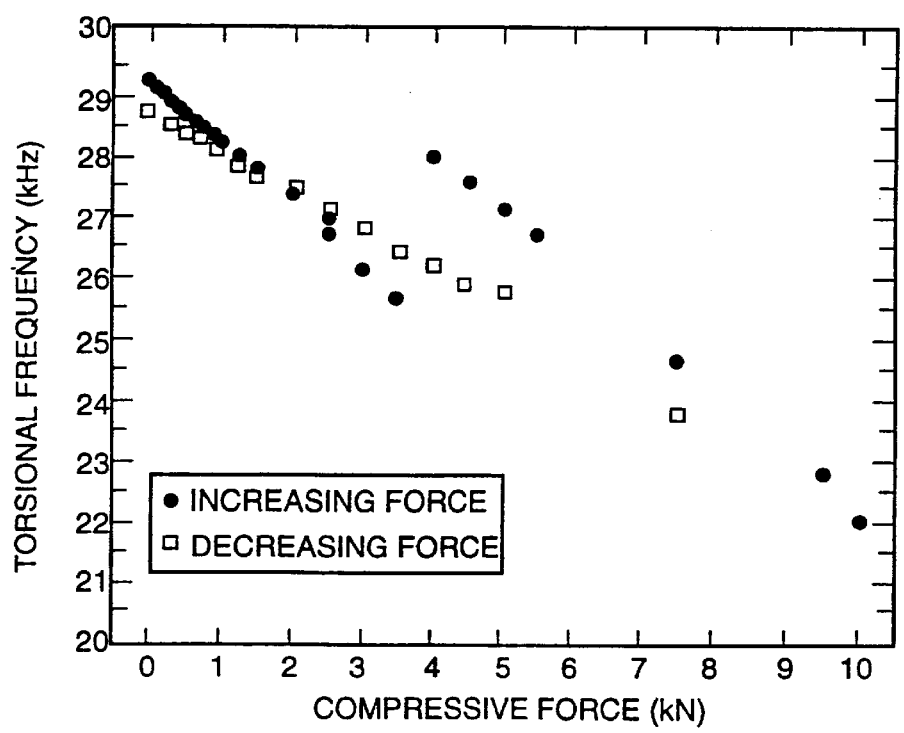
FIG. 14 is a chart showing the relationship between the resonant torsional frequency and the magnitude of an axial load placed on a cylindrical object.
Figure 15:
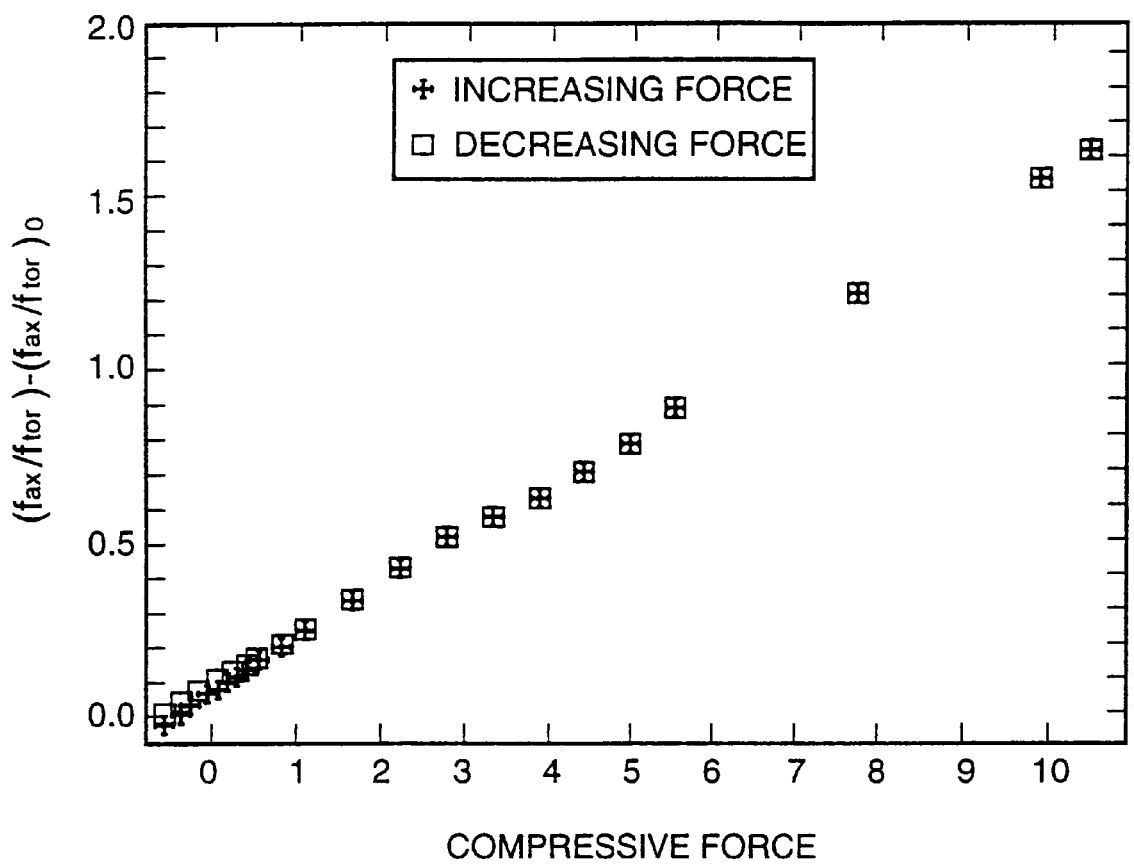
FIG. 15 is a chart showing the relationship between the ratio of the resonant axial shear frequency to the resonant torsional frequency and the magnitude of an axial load applied to a cylindrical object.

Methods for determining the loading applied to the cylindrical object 32 using the EMATs 30 are described in reference to FIGS. 13–15. The loading could be an axially compressive or tensile load, or in the case of tubes, the loading could be a pressure applied to the interior of the tube.

As in the method for temperature determination, the amount of loading applied to the cylindrical object 32, affects the frequency at which it experiences resonant vibrations. The simplest way to determine the magnitude of loading applied to the cylindrical object 32 is to use the EMAT 30 to determine the resonant frequencies of the cylindrical object 32 at various different magnitudes of loading. First, the EMAT 30 is used to determine a resonant frequency of the cylindrical object 30 when no loading is applied. A first load is then applied to the cylindrical object and the EMAT 30 is used to determine the new resonant axial shear frequency. This process is repeated for a number of different loads to determine the resonant frequencies at each load.

The test data is then used to prepare a chart showing the relationship between the magnitude of the load and the resonant frequency. FIG. 13 shows the relationship between a resonant axial shear frequency of the cylindrical object 32 and a compressive load applied to the cylindrical object 32. FIG. 14 shows the relationship between a resonant torsional frequency of the cylindrical object 32 for the same range of compressive forces. Once these charts have been constructed one can use the EMAT 30 to determine the resonant frequency. The chart is then used to determine the magnitude of the load.

Unfortunately, temperature has a great affect on the resonant frequency of the cylindrical object J2. The resonant frequencies plotted in FIGS. 13 and 14 were measured concurrently by two different EMATs 30 as a compressive load applied to the cylindrical object 32 was sequentially increased (black dots), then sequentially decreased (hollow squares). The sudden jump in the resonant frequencies for both axial shear and torsional vibration between 3 and 4 kN that occurred when the forces were being increased (the black dots) is the result of a small (a few degrees Celsius) temperature change in the testing room between measurements.

Because of the affect of temperature on the resonant frequencies, the charts shown in FIGS. 13 and 14 are only useful for a relatively narrow temperature range. To determine the loading with an acceptable level of accuracy using a single resonant frequency chart, as shown in FIGS. 13 or 14, the original testing done to create the charts, and the actual test of the loading, must be performed at the same temperature.

A second method for determining the load, however, accounts for temperature variations. In this method, an unloaded cylindrical object is first tested to determine a particular resonant axial shear frequency and a particular resonant torsional frequency. Next, measurements of the resonant frequencies are taken for a number of different magnitudes of load for the two different modes of vibrations. As described above, the charts of FIGS. 13 and 14 will result from the measurements.

Next, a ratio is calculated, representing the resonant axial shear frequency to the resonant torsional frequency for the cylindrical object 32 with no load applied. Then, a plurality of different ratios are calculated representing the resonant axial shear frequency divided by the resonant torsional frequency for each of the different compressive forces applied to the cylindrical object 32. A plurality of difference measurements are then calculated representing the difference between the no load ratio, and the each of the loaded ratios.

The ratios are then plotted as shown in FIG. 15. As shown in FIG. 15, a relatively straight line will result showing the relationship between the compressive force and the difference between the two ratios. The temperature variation occurring between the 3 and 4 kN measurements does not affect the difference in the ratios. This method can be used to account for temperature variations in determining the magnitude of loading on the cylindrical object 32, so long as temperature variations affect each type of resonant frequency approximately equally.

Once a plot as shown in FIG. 15 is produced for a particular cylindrical object 32, the amount of a force applied to the cylindrical object 32 can be determined by measuring the axial shear and torsional resonant frequencies, calculating a ratio between the resonant frequencies, and comparing the calculated ratio to the no load ratio.

As mentioned above, the same method can be used to determine the magnitude of a tensile load applied to the cylindrical object 32. If the cylindrical object 32 is a hollow tube, this method can also be used to determine a pressure within (or without) the tube.

When a symmetrical EMAT 30 having only two magnets 22 (one on each side of the cylindrical object 32) is used to determine the resonant frequency of the cylindrical object 32, at some frequencies ranges, instead of getting a response signal with a single large amplitude spike at a single resonant frequency, two smaller amplitude signals are sensed at two slightly separated resonant frequencies. It is believed that the splitting of the resonant frequencies is due to the grain orientation of the material comprising the cylindrical object 32. This resonant frequency splitting can be exploited to determine the grain orientation of the material of the cylindrical object 32 using the method described below.

In a first step, the cylindrical object 32 is inserted to the EMAT 30 having two evenly spaced magnets 22. The cylindrical object 32 is oriented at a first rotational position, and the amplitude of a response signal of the wire coil of the EMAT 30 is recorded for each of two closely spaced resonant frequencies. Next, the cylindrical object 32 is rotated a certain number of degrees and the amplitudes of response signals are again recorded for each of the two split resonant frequencies. This procedure may be repeated for a plurality of different rotational positions of the cylindrical object 32. By comparing the amplitudes of the response signals at the different rotational positions, the grain orientation of the material which forms the cylindrical object 32 can be determined.

In addition to determining grain orientation, the same basic method can be used to determine variations in the thickness of thin walled tubing around the circumference of the tube. If the amplitudes of the split resonant frequencies remain relatively constant as the tube is rotated in the EMAT 30, the wall thickness is relatively constant. Variations in the amplitude indicates variations in the wall thickness.

The use of the EMAT 30 having two magnets 22 in the above described method is not essential to the method. All that is required is that the EMAT 30 produce a split resonant frequency response signal.

The texture of the cylindrical object 32 can also be determined by measuring the elastic constant of the cylindrical object 32 for axial shear vibrations and torsional vibrations, and comparing the measurements. The comparison of the elastic constants at various rotational positions will also provide an indication of the grain orientation of the material in the cylindrical object 32.

Variations in the above-described methods can be used to determine a variety of different physical properties of the cylindrical object 32 using EMATs 30 according to this invention.

While this invention has been described in conjunction with specific embodiments thereof, it is evident that many alternatives, modifications, and variations will be apparent to those skilled in the art. Accordingly, it is intended to embrace all such alternatives, modifications and variations as fall within the spirit and scope of the appended claims.

What is claimed is:

1. An electromagnetic acoustic transducer, comprising:
    a housing having a circular opening surrounding an exterior circumferential wall of a cylindrical object inserted into the housing;
    a plurality of magnets mounted in the housing and arranged around the circular opening at evenly spaced intervals, each magnet having an end adjacent the circular opening, the ends of adjacent magnets having opposite polarities;
    at least one electrically conductive wire coil mounted in the housing adjacent the ends of the plurality of magnets, wherein the at least one wire coil forms a cylindrical shape surrounding the circular opening;
    a signal generator connected to the at least one wire coil and supplying an electrical excitation signal to the at least one wire coil to induce vibrations in the cylindrical object; and
    a signal detector connected to the at least one wire coil and detecting an electrical response signal induced in the at least one wire coil by vibrations in the cylindrical object.

2. The electromagnetic acoustic transducer of claim 1, wherein the electrical excitation signal applied to the at least one wire coil induces axial shear vibrations in the cylindrical object.

3. An electromagnetic acoustic transducer, comprising:
    a cylindrical object;
    a plurality of magnets arranged radially about the cylindrical object at substantially equal intervals, wherein ends of adjacent magnets having opposite polarities; and
    a electrically conductive wire coil wound around the cylindrical object in the form of a solenoid coil and radially positioned between the ends of the plurality of magnets and the cylindrical object.

4. The electromagnetic acoustic transducer of claim 3 further comprising:
    an electrical excitation signal flowing in the electrically conductive wire coil; and
    Lorentz forces induced in the cylindrical object by the electrical excitation signal wherein the Lorentz forces are oriented in the axial direction of the cylindrical object.

5. The electromagnetic acoustic transducer of claim 4, wherein at any point along an axially oriented line intersecting the electrically conductive wire coil the electrical excitation signal comprises a current that at any point in time runs in a single direction relative to the cylindrical object.

6. A transducer comprising:

a cylindrical object;

a first set of magnetic poles arranged about the cylindrical object and having a substantially uniform spacing between adjacent ones of the first set of magnetic poles;

a second set of magnetic poles having an opposite polarity from the first set of magnetic poles arranged about the cylindrical object such that each of the first set of poles is separated by one of the second set of poles;

a conductive loop wherein the center of the loop is aligned with the center of the cylindrical object and the loop is positioned in the space between the first and second sets of poles and the cylindrical object;

an excitation signal flowing in the conductive loop and operable to induce vibrations in the cylindrical object; and a response signal induced in the conductive loop by the vibrations in the cylindrical object.

7. The transducer of claim 6 wherein the induced vibrations comprise axial shear vibrations.

8. The transducer of claim 6 wherein the induced vibrations are associated with Lorentz forces induced in the cylindrical object by the excitation signal.

9. The transducer of claim 6 wherein the excitation signal comprises a flow of electrical charge in the conductive loop.

10. The transducer of claim 6 wherein the response signal comprises a flow of electrical charge in the conductive loop.

11. The transducer of claim 10 wherein at any point in time the electrical charge flows in a single direction relative to the cylindrical object.

12. The transducer of claim 6 wherein the conductive loop comprises a metal wire wound about the cylindrical object.

13. The transducer of claim 6 wherein the conductive loop comprises a wire coil wound about the cylindrical object in the form of a solenoid coil.

14. The transducer of claim 6 further comprising a signal generator coupled to the conductive loop so as to drive an electrical charge having alternating directions in the conductive loop.

15. The transducer of claim 14 wherein the signal generator comprises an adjustable frequency signal generator.

* * * * *